(12) United States Patent
Huang et al.

(10) Patent No.: US 12,742,790 B2
(45) Date of Patent: Sep. 22, 2026

(54) REMOVABLE REAGENT PACK FOR USE IN IN-VITRO DIAGNOSTIC DEVICE AND METHOD FOR CONTROLLING THE SAME

(71) Applicant: EDAN INSTRUMENTS, INC., Shenzhen (CN)

(72) Inventors: Gaoxiang Huang, Shenzhen (CN); Zhixiang Zhao, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 512 days.

(21) Appl. No.: 18/343,724

(22) Filed: Jun. 28, 2023

(65) Prior Publication Data

US 2023/0349930 A1 Nov. 2, 2023

Related U.S. Application Data

(63) Continuation of application No. PCT/CN2021/143218, filed on Dec. 30, 2021.

(30) Foreign Application Priority Data

Dec. 31, 2020 (CN) ......................... 202011635731.5

(51) Int. Cl.
*G01N 33/72* (2006.01)
*G01N 35/10* (2006.01)

(52) U.S. Cl.
CPC ......... *G01N 33/721* (2013.01); *G01N 33/726* (2013.01); *G01N 35/1009* (2013.01)

(58) Field of Classification Search
CPC ............... G01N 33/721; G01N 33/726; G01N 35/1009; G01N 2035/00148; G01N 2035/00306; G01N 35/00; G01N 35/00584; G01N 2035/00178; B01L 2200/025; B01L 2200/16; B01L 2300/0627; B01L 3/502
See application file for complete search history.

(56) References Cited

FOREIGN PATENT DOCUMENTS

| | | | |
|---|---|---|---|
| CN | 103543192 | A | 1/2014 |
| CN | 106290493 | A | 1/2017 |
| CN | 109557295 | A | 4/2019 |
| CN | 111257548 | A | 6/2020 |
| CN | 111562286 | A | 8/2020 |

OTHER PUBLICATIONS

International Search Report,International Application No. PCT/CN2021/143218, mailed Mar. 21, 2022 (11 pages).
European Search Report, European Patent Application No. 21914662.8, mailed May 22, 2024 (9 pages).
Chinese First Office Action, Chinese Application No. 202011635731.5,mailed Apr. 9, 2026(17 pages).

*Primary Examiner* — Christine T Mui

(57) ABSTRACT

The present application provides a removable reagent pack for use in an in-vitro diagnostic device. The removable reagent pack internally includes a calibration solution bag, a calibration solution output pipeline, a valve part, a pump, and an air pipeline, wherein the calibration solution output pipeline is connected to a first end of the valve part, the air pipeline is connected to a second end of the valve part, and a third end of the valve part is connected to an external interface of the reagent pack by means of the pump. The removable reagent pack is suitable for independent transportation and storage, and the reagent pack can be reused many times because the readable device is provided with a device allowing for reading factory information and use status.

20 Claims, 6 Drawing Sheets

REMOVABLE REAGENT PACK FOR USE IN IN-VITRO DIAGNOSTIC DEVICE AND METHOD FOR CONTROLLING THE SAME

CROSS-REFERENCE TO RELATED APPLICATIONS

The present application is a continuation of International (PCT) Patent Application No. PCT/CN2021/143218 filed on Dec. 30, 2021, which claims priority to Chinese patent application No. 202011635731.5, filed on Dec. 31, 2020, the contents of all of which are hereby incorporated by reference.

TECHNICAL FIELD

The present disclosure relates to the field of in-vitro technologies, and more particularly, to a removable reagent pack for use in an in-vitro diagnostic device.

BACKGROUND

The determination of gas component in blood is very important in various scientific researches and practical applications. In the rescue of critical clinical medicine patients, rapid and continuous determination of the partial pressure of blood carbon dioxide is critical. Especially for mechanically ventilated patients, blood carbon dioxide partial pressure is a key index for judging respiratory state of patient, and various parameters of the breathing machine are mainly set according to the partial pressure of carbon dioxide in the blood of the patient. At present, the most widely used blood gas component detector in medicine is a blood gas analyzer, but the conventional blood gas analyzer has the defects that a large number of blood samples need to be collected, the detection is discontinuous, the detection result is lagged, and the like.

The traditional in-vitro blood gas detection is performed in a large test center with good equipment. Although these conventional test centers can provide efficient and accurate testing of large volume fluid samples, it is not possible to provide a direct result. The practitioner must collect the fluid sample, send it to the laboratory, then the fluid sample is processed by the laboratory, and finally, the result is conveyed the patient. This traditional detection method causes a long and complex cycle of blood gas testing, it is difficult for patients to obtain timely diagnostic results, which is not conducive to timely diagnosis by medical staff and cannot provide patients with a good medical experience.

In addition, conventional in-vitro diagnostic testing requires training laboratory technicians to perform the test, thereby ensuring the accuracy and reliability of the test. However, usage errors caused by personnel handling samples may lead to surface contamination, sample spillage, or damage to diagnostic devices, resulting in increased repair and maintenance costs.

At the same time, in the related art, the reagent pack for in-vitro diagnosis is usually placed inside a test card or a host of an in-vitro diagnosis system. It is not convenient for operators to replace and is also prone to waste.

SUMMARY OF THE DISCLOSURE

A removable reagent pack for use in an in-vitro diagnostic device includes a housing, at least one external interface, at least one liquid storage device, at least one transport control device, and at least one positioning mechanism. The at least one external interface is located on the housing, the at least one liquid storage device includes an output pipeline, and the at least one liquid storage device is located in a space formed by the housing. The at least one transport control device is located in the space. The at least one transport control device is configured to control at least a flow direction in a pipeline inside of the removable reagent pack, so that a liquid inside of the at least one liquid storage device flows out through the output pipeline. The at least one positioning mechanism is connected to the at least one transport control device, so that the at least one transport control device is driven by an in-vitro diagnostic device.

In some embodiments, the transport control device is a pump.

In some embodiments, the pump is configured to be forward rotation and/or reverse rotation.

In some embodiments, the pump is a peristaltic pump.

In some embodiments, the removable reagent pack further includes at least one pipeline switching device.

In some embodiments, the removable reagent pack further at least includes three pipelines: a first pipeline being the output pipeline of the liquid storage device, a second pipeline connected to an exterior, and a third pipeline connected to the external interface of the removable reagent pack; wherein the pipeline switching device is configured to allow one of the first pipeline and the second pipeline to connect to the third pipeline.

In some embodiments, the transport control device is located on at least a third pipeline.

In some embodiments, the at least one external interface is configured to output output gas and/or input gas in the removable reagent pack.

In some embodiments, the external interface is at least partially encapsulated with a seal.

In some embodiments, the liquid is a calibration liquid.

In some embodiments, the positioning mechanism is a groove, and/or the pipeline switching device is a three-way valve.

In some embodiments, the removable reagent pack further includes a readable device for recording status information, wherein the status information includes one or more of the liquid type, usage temperature, capacity, adapted sensor type, historical usage status of the removable reagent pack, and current capacity status information.

A method for controlling a removable reagent pack, including: a first stage, configuring a transport control device to allow a removable reagent pack to outwardly output quantitative calibration liquid; a second stage, configuring the transport control device to allow the removable reagent pack to outwardly output a quantitative gas; a third stage, configuring the transport control device to allow the exterior to input the quantitative gas into the removable reagent pack; and a fourth stage, configuring the transport control device to allow the removable reagent pack to outwardly output the quantitative gas.

In some embodiments, the first stage is a stage that a sensor is calibrated by a test card or a blood gas analyzer host.

In some embodiments, the second stage is a stage of emptying the calibration liquid after completing a calibration.

In some embodiments, third stage is a stage that a sample to be detected is injected into a test card for blood gas detection.

In some embodiments, the fourth stage is a stage that a sample to be detected in the test card is transferred from a blood gas detection area to a hemoglobin and its derivatives detection area.

In some embodiments, based on the same sample to be detected in a test card, a blood gas detection is performed in the third stage, and a detection of hemoglobin and its derivatives is performed in the fourth stage.

In some embodiments, in the first stage, the second stage and the fourth stage, the transport control device is configured to receive a forward driving force output by a host of an in-vitro diagnostic device; and in the third phase, the transport control device is configured to receive a reverse driving force output by the host of the in-vitro diagnostic device.

In some embodiments, in the first stage, a pipeline switching device in the removable reagent pack is configured to connect an output pipeline of a liquid storage device to at least one external interface; and in the second stage to the fourth stage, the pipeline switching device is configured to connect a gas source to the at least one external interface.

DETAILED DESCRIPTION

Figure 1:
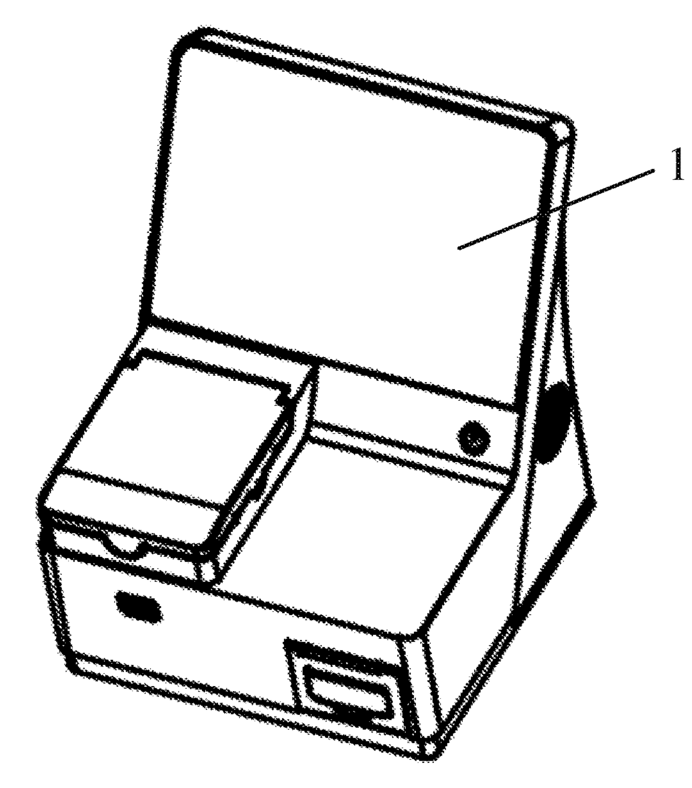
FIG. 1 is a schematic view of an external structure of an in-vitro medical diagnostic system.

In view of the foregoing, a purpose of the present disclosure is providing a removable reagent pack for use in an in-vitro diagnostic device, and the removable reagent pack is capable of at least partially mitigating or eliminating at least one defect in the related art.

It is very necessary to arrange a removable reagent pack for use in the in-vitro diagnostic device. The removable reagent pack can be independently of the test card and the in-vitro diagnosis system, independently transported and stored, and can be matched with the test card to realize blood gas detection operation.

The present disclosure will now be further described in conjunction with the accompanying drawings and specific embodiments.

Before turning to the drawings illustrating exemplary embodiments in detail, it is to be understood that the present disclosure is not limited to the details or methods shown in the specification or illustrated in the drawings. The purpose of professional terminology is only for illustration and should not limit the understanding of present product and corresponding methods.

Figure 2:
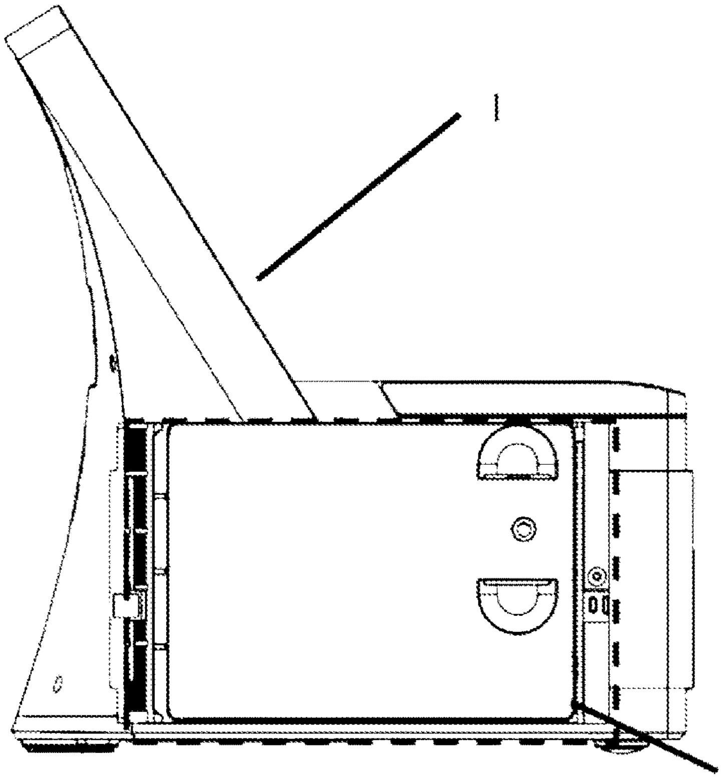
FIG. 2 is a schematic side view of the in-vitro medical diagnostic system.
Figure 3:
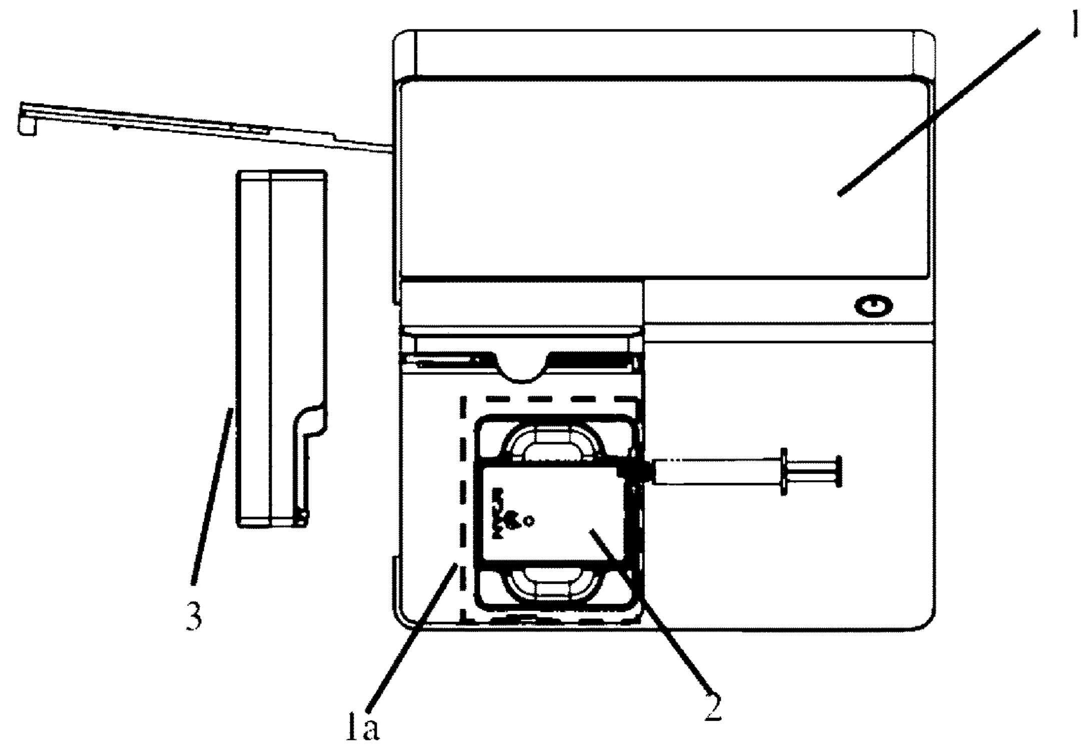
FIG. 3 is a schematic view of a combination of components of the in-vitro medical diagnostic system.

Exemplary embodiments of the present disclosure provide an in-vitro medical diagnostic system. As shown in FIGS. 1-3, the in-vitro medical diagnostic system includes a host 1, removable test card 2, and a removable reagent pack 3. The host 1 includes a housing, and processing circuitry, a power supply circuitry and optical elements located in the housing. The housing further includes a first area 1*a* configured to at least partially accommodate the removable test card 2, and a second area 1*b* configured to at least partially accommodate the removable reagent pack 3. The removable test card 2 is jointed with the host 1 and the removable reagent pack 3 through the first area 1*a* and the second area 1*b*, respectively, such that there is no fluid communication between the removable test card 2 and the host 1, and there is no fluid communication between the removable reagent pack 3 and the host 1.

Removable Test Card

The removable test card 2 includes an external interface, a detection area, a waste liquid area, a liquid path control area and an internal liquid path.

The external interface refers to a first interface for receiving fluid samples, a second interface for air pump inlet/outlet, and a third interface for injecting calibration liquid located on the sides, top, or bottom of the test card 2. Specifically, a fluid sample inlet is on the first side of the test card 2. The fluid sample inlet is configured to receive fluid samples, such as whole blood samples that do not require homolysis. A calibration liquid inlet and an exhaust port are on the second side of the test card 2. The calibration liquid inlet is configured to receive calibration liquid from the outside (such as the removable reagent pack 3) for calibration of various photochemical sensors inside the test card 2. The exhaust port is configured to be connected to the external atmosphere to maintain pressure balance in the test card 2, in order to ensure that the calibration liquid or fluid sample flows into the test card 2.

The detection area refers to the area where electrical, optical, chemical sensors and/or cavities without sensors are placed for detecting various blood gas parameters. The detection of blood gas, hemoglobin, electrolytes, and other biochemical parameters is completed in this area.

The waste liquid area refers to the area configured to store the detected fluid samples.

The internal liquid path refers to the pipeline path configured to allow the fluid sample or calibration liquid to flow inside of the test card 2. The pipeline path has multiple interconnected liquid paths, and the detection area, the waste liquid area, and the liquid path control area are located on different liquid paths.

The liquid path control area refers to the area, where several on-off control devices are located. The on-off control devices are configured to control the on-off of the internal liquid path, thereby achieving liquid path switching, allowing the calibration liquid and fluid samples at different testing stages to flow into the detection area and waste liquid area through different paths. The detailed switching operation will be described in detail later.

The detection area, the waste liquid area and the liquid path control area are generally located between the first side and the second side of the test card 2.

Each functional area and the internal liquid path of the test card 2 have a plurality of implementation modes, and one of the preferred implementation modes is provided as follows.

Figure 4:
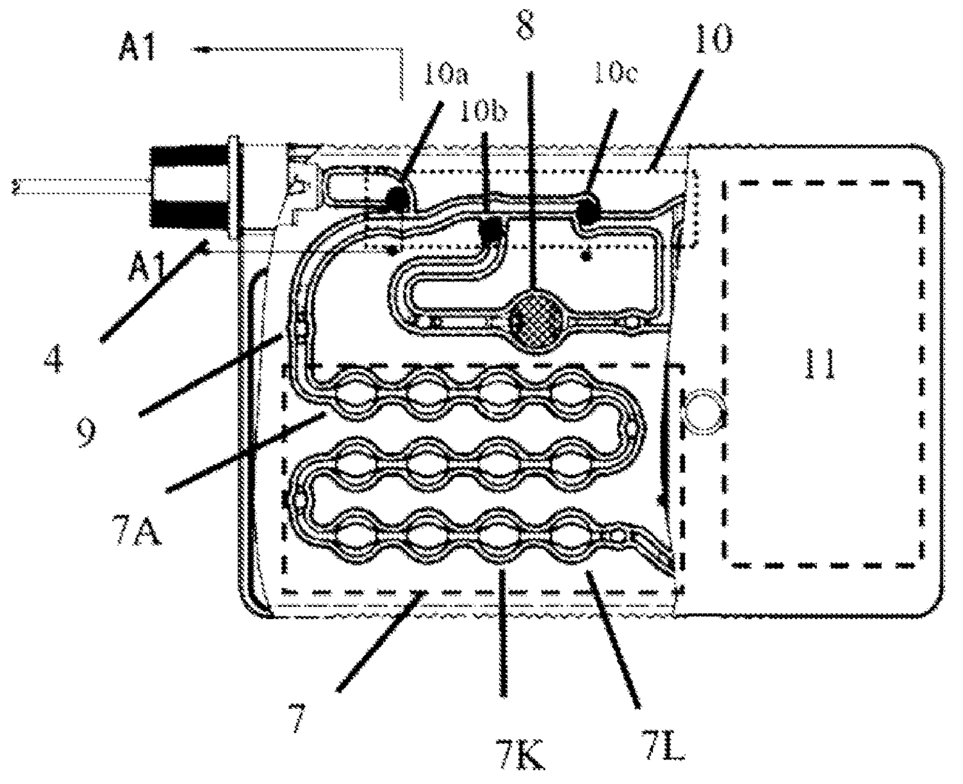
FIG. 4 is a schematic semi-sectional view of a removable test card.
Figure 5:
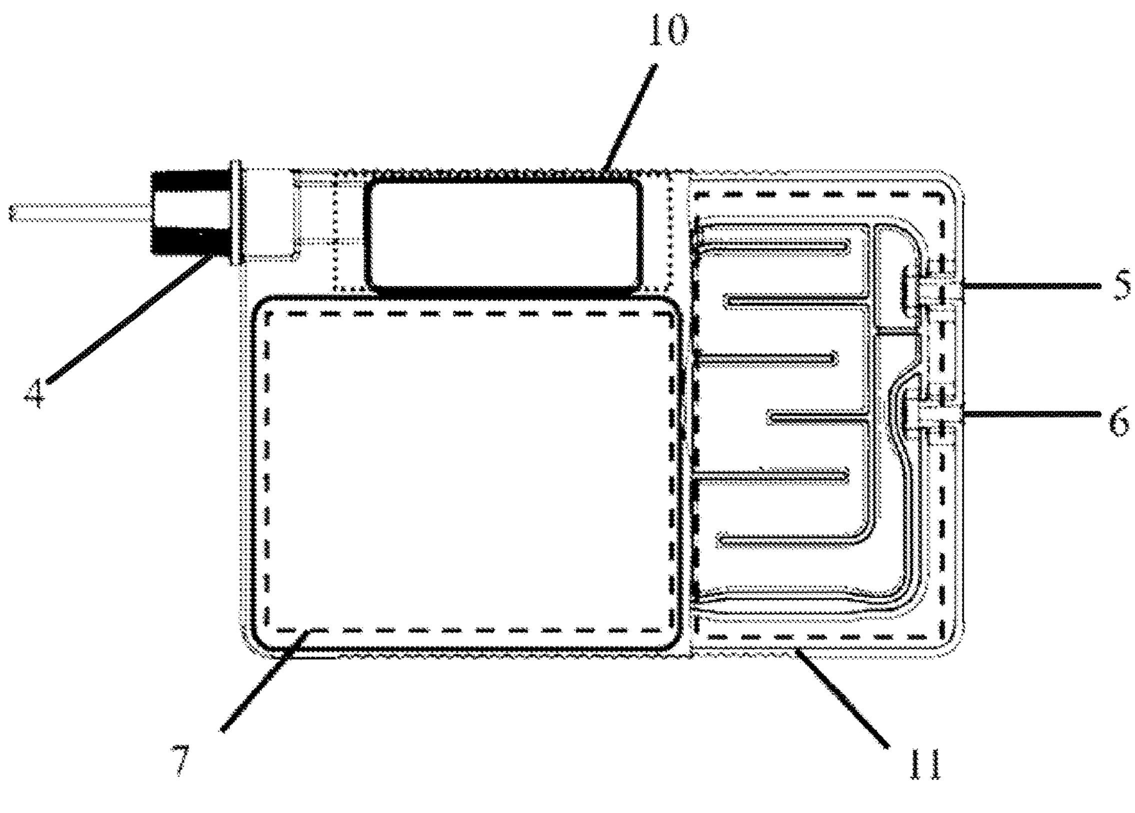
FIG. 5 is another schematic semi-sectional view of the removable test card.
Figure 6:
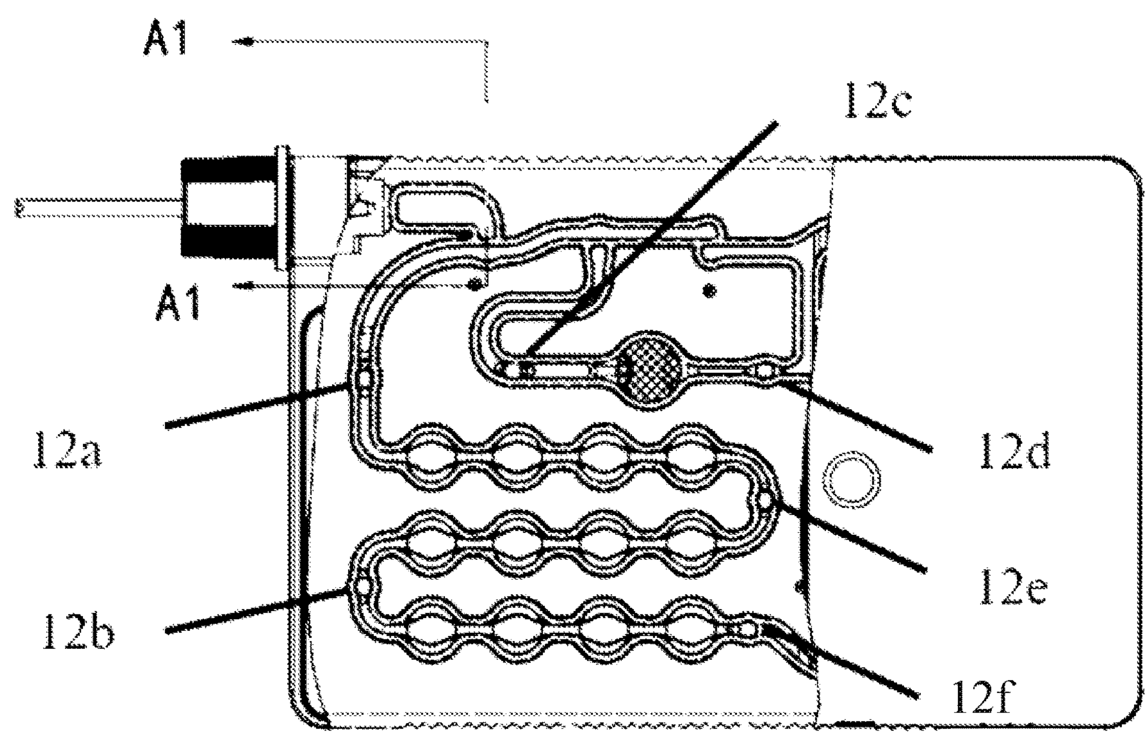
FIG. 6 is yet another schematic semi-sectional view of the removable test card.
Figure 7:
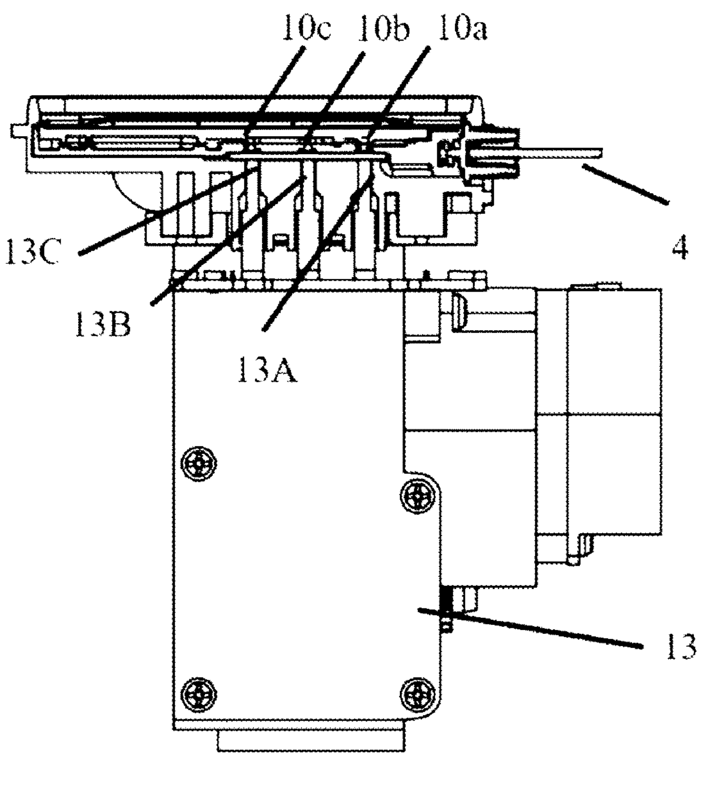
FIG. 7 is a schematic view of the connection of the removable test card and a valve control device.

As shown in FIGS. 4-6, the removable test card 2 includes a card body, at least one portion of the card body is transparent. The card body may be made of molded plastic, additional material, or sets of materials. In order to better reflect the division of the transparent housing and internal functional areas of the card body, the semi-sectional views in FIGS. 4-6 are used to show the housing and internal functional areas of the test card 2.

The fluid sample to be detected is a blood sample. In an embodiment, the fluid sample is a whole blood sample without hemolysis. The detection area includes a blood gas detection area 7 and a hemoglobin and its derivatives detection area 8. The waste liquid area 11 is configured to store the detected blood sample. The internal liquid path 9 is divided into a main liquid path and three controllable liquid paths. The main liquid path is connected to the calibration liquid inlet 6, the blood gas detection area 7 and the liquid path control area 10. In an embodiment, the blood gas detection area 7 is between the calibration liquid inlet 6 and the liquid path control area 10. The first controllable liquid path is configured to control the on-off of the liquid path between the sample inlet 4 and the main liquid path. The second controllable liquid path is configured to control the on-off of the liquid path between the main liquid path and the inlet of the hemoglobin and its derivatives detection area 8, and the outlet of the hemoglobin and its derivative detection area 8 is communicated to the waste liquid area 11. The third controllable liquid path is configured to on-off the waste liquid area 11 and the main liquid path. The waste liquid area 11 is connected to the exhaust port 5. The blood gas control area and the second controllable liquid path are arranged with several position detection points. The liquid path control area 10 is provided with three valves 10*a* to 10*c* for controlling the on-off of the internal liquid path 9, respectively configured to control the first, second and third controllable liquid paths. The control mode will be described in detail in the following sections.

The blood gas detection area 7 has twelve sensor cavities defined as 7A to 7L, the cavities are sequentially arranged on the main liquid path. The cavity may be of various shapes, and the shapes of the cavities can be the same or different. However, in the flow direction of the liquid path, the width of the sensor cavity is wider than the width of the liquid path. Various types of sensors can be placed in the cavity. The twelve sensor cavities are arranged from far to near according to the distance from the calibration liquid inlet in the direction of the flow path, sequentially numbered 7A-7L. The first eleven sensor cavities 7A-7K are sequentially provided with different photochemical sensors, the twelfth sensor cavity 7L is used as a standby for future detection parameter expansion, and the hemoglobin and its derivatives detection area 8 is only a cavity and is not provided with a sensor.

In an embodiment, the photochemical sensors in each of the first ten sensor cavities 7A-7J are configured to detect the blood gas parameters in the blood fluid sample, such as $CO_2$, $O_2$, pH, $Na^+$, $M^{++}$, or the like.

In an embodiment, the fluid sample can be a whole blood sample, a urine sample and other types of human body fluid samples, and in this case, the sensor in the test card 2 detects corresponding biochemical parameter indexes.

The control mode of the test card 2 is described in detail below.

Before detecting the blood samples, it is necessary to calibrate all sensors in test card 2, that is, inject calibration liquid into the sensor, empty all calibration liquid in test card 2 after calibration, and then inject fluid samples to be detected. In an embodiment, the fluid samples are blood samples that do not require hemolysis. The testing is completed in the detection area, and the corresponding parameters are read through the host of the in-vitro medical diagnosis system. After completing the diagnostic analysis, the corresponding parameters and diagnostic results are displayed on the host screen, so that medical personnel can timely learn about the corresponding situation.

The specific operation steps are as follows:

operation S1: placing the test card 2 into the first area 1*a;* operation S2: pumping the calibration liquid into the detection area in the test card 2;

operation S3: after finishing calibration, transferring the calibration liquid in the test card 2 to the waste liquid area 11 in the test card 2;

operation S4: injecting blood sample into the detection area to complete the detection of at least hemoglobin and blood gas in the detection area; and operation S5: transferring the blood sample in the detection area to the waste liquid area 11 in the test card 2 to complete the detection.

The operation S1 specifically includes as follows. Before the test card 2 is jointed with the reagent pack 3 and the host 1, the test card 2 is internally dry and has no calibration liquid. The calibration liquid is stored in the reagent pack 3, separated from the test card 2. The detection, position is the first area 1*a* in the host 1. When the test card 2 is placed in the first area 1*a*, the fluid sample in the test card 2 is detected. As shown in FIG. 6, at least six position detection points 12*a* to 12*f* are arranged in the test card 2 and can receive light intensity emitted by a detection light source and transmitted through the test card 2, so that whether liquid exists at the position detection points 12*a* to 12*f* or not can be detected and judged.

The operation S2 specifically includes as follows. The third controllable liquid path is communicated, the first and second controllable liquid paths are controllably closed. The host 1 controls the peristaltic pump 16 and the three-way valve 17 in the reagent pack 3, switching the three-way valve 17 to the calibration liquid pipeline 19, pumping the calibrating liquid (i.e., standard sample liquid with known composition and concentration in the calibration liquid bag 15 into the test card 2 through a connecting piece 20 inserted into the calibrating liquid inlet of the test card 2. When the position detection point 12*a* detects that liquid exists, the host 1 controls the peristaltic pump 16 in the reagent pack 3 to stop moving, at the moment, the sensor cavities 7A to 7K are filled with the calibration liquid. The host 1 starts calibrating the sensors reading the readings of the liquid sensors of the standard sample measured by the sensors), and the host 1 finishes calibrating after reading the detection values of the sensors.

The operation S3 specifically includes as follows. The third controllable liquid path is kept communicated, and the first and second controllable liquid paths are kept closed. The host 1 controls the three-way valve 17 in the reagent pack 3 to be switched to the air channel. The peristaltic pump 16 is controlled to pump the air into the test card 2 through the connecting piece 20 inserted into the calibration liquid inlet of the test card 2. Because the waste liquid area 11 of the test card 2 is connected to the outside air through the exhaust port 5, with the pumping of the air, the calibration liquid continuously moves to the waste liquid area 11 in the first and third liquid paths until all the calibration liquid enters the waste liquid area 11.

The operation S4 includes two stages, i.e., a first stage and a second stage as follows.

The blood gas detection is performed in the first stage. Specifically, the first controllable liquid path is communicated, the second and third controllable liquid paths are closed, and the blood gas detection is performed in this case. The blood sample is injected from the sample inlet 4 of the test card 2, without hemolysis, or the host 1 controls the peristaltic pump 16 to rotate reversely, extracting the air in the test card 2, negative pressure is generated in the test card 2 to suck blood at the sample inlet 4 into the test card 2. Thus, after it is determined by the position detection points 12*a* to 12*f* that the blood sample to be detected completely enters the sensor cavities 7A to 7L, stopping injecting the blood sample to be detected into the test card 2, alternatively, the host 1 controls the peristaltic pump 16 to stop pumping air, and the blood sample is detected by using the sensor cavities 7A to 7L. In an embodiment, the photochemical sensors are arranged in the sensor cavities 7A to 7K, the sensor cavity 7L is used as standby sensors or other types of sensors are placed in the sensor cavity 7L.

The basic detection principle of the photochemical sensor is that the photochemical method uses organic dyes to emit fluorescence with different wavelengths from the irradiation light under specific wavelengths of light, influenced by substances such as $O_2$ and $CO_2$ concentration and pH. The fluorescence is transmitted to the detector to detect its fluorescence signal and perform quantitative analysis, thereby being able to detect $O_2$, $CO_2$, and pH values.

Entering the second stage after completing blood gas detection, that is, hemoglobin and its derivatives are detected. The first controllable liquid path is kept communicated and the third controllable liquid path is kept closed, the second controllable liquid path is opened. The host 1 controls the peristaltic pump 16 to rotate forward, pumping air into the test card 2, so that the blood in the blood gas detection area is sent into the hemoglobin and its derivative detection area 8 through the second controllable liquid path. Then the host 1 controls the peristaltic pump 16 to stop pumping air into the test card 2, using the light emitted from the first light source to irradiate the hemoglobin and its derivative detection area 8 from one side, and receiving the transmitted light from the other side of the hemoglobin and its derivative detection area 8 to detect whether hemoglobin and its derivative are present in the blood sample or not according to the detection principle of colorimetric method.

The operation S5 specifically includes as follows. After completing the detection of hemoglobin and its derivative, the host 1 controls the peristaltic pump 16 to rotate forward and pumps air into the test card 2 to push the blood sample in the hemoglobin and its derivative detection area 8 into the waste liquid area 11. After the blood sample enters the waste liquid area 11, the host 1 controls the peristaltic pump 16 to stop rotating and the test is finished.

In the above steps, the control of the first, second and third controllable liquid paths is realized as shown in FIG. 7 and FIG. 8A-8D.

Three valves 10*a* to 10*c* are inside of the liquid path control area 10. The valves 10*a* to 10*c* are respectively configured to control the on-off of the first, second and third controllable liquid paths, and the on-off of the valves 10*a* to 10*c* are respectively driven by the control mechanisms 13A to 13C in the valve control device 13. When one of the control mechanisms 13A to 13C moves downwards, one corresponding valve in the valves 10*a* to 10*c* is opened, and the corresponding controllable liquid path is conductive. Otherwise, when one of the control mechanisms 13A to 13C moves upwards to the end, one corresponding valve in the valves 10*a* to 10*c* is closed, and the corresponding controllable liquid path is not conductive.

Figure 8A:
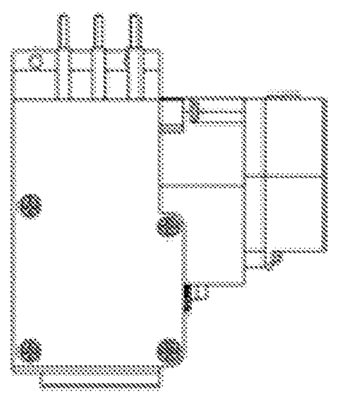
FIG. 8A is a schematic control view of the valve control device.
Figure 8A:

Specifically, in the operation S1, the valves 10*a* to 10*c* are all in a closed state, and the positions of the control mechanisms are shown in FIG. 8A, that is, the first, second and third controllable liquid paths are all disconnected.

Figure 8B:
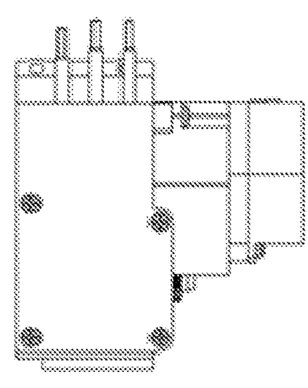
FIG. 8B is another schematic control view of the valve control device.

In the operations S2 and S3, the valves 10*a* to 10*b* are in the closed state, the valves 10*c* are in a conductive state, the positions of the control mechanisms are shown in FIG. 8B, and the main liquid path is connected to the waste liquid area 11, so that the calibration liquid can be pumped into the test card 2. After completing calibration, air is pumped into the test card 2, so that the calibration liquid enters the waste liquid area 11.

Figure 8C:
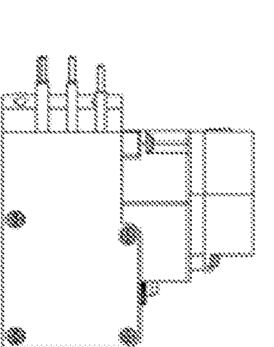
FIG. 8C is yet another schematic control view of the valve control device.

In the first stage of the operation S4, the valve 10*a* is controlled to be conductive, the valves 10*b* to 10*c* are in the closed state, the positions of all the control mechanisms are shown in FIG. 8C, and the main liquid path is connected to the sample inlet 4, so that the blood sample can be injected into the test card 2, and the sample blood reaches the blood gas detection area 7 for blood gas detection.

Figure 8D:
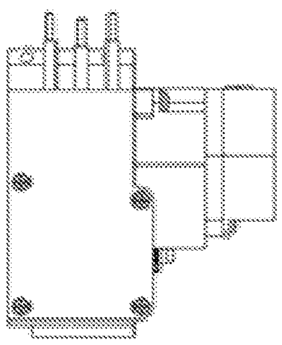
FIG. 8D is yet another schematic control view of the valve control device.

In the second stage of operation S4, that is, after the blood gas detection is completed, the valve 10*b* is controlled to be conductive, and the valves 10*a* and 10*c* are in the closed state. The positions of the control mechanisms are shown in FIG. 8D, the main liquid path is connected to the hemoglobin and its derivatives detection area 8, so that the blood sample can enter the hemoglobin and its derivatives detection area 8, and the detection of the hemoglobin and its derivatives is performed.

After the detection is completed, the blood sample is sent into waste liquid area 11.

The turn-off sequence of the valves 10*a* to 10*c* may be set to a fixed timing sequence or customized and logically programmed according to the needs of the operator.

In an exemplary embodiment, the widths of the first, second and third liquid paths may be set to be different. In an embodiment, the width of the second liquid path is greater than the width of the first liquid path. The thickness of the sensor cavity of the test card 2 in the blood gas detection area 7 is different from the thickness of the cavity in the hemoglobin and its derivative detection area 8, so as to meet the requirements of blood gas photochemical detection of whole blood sample and different detection methods of hemoglobin and its derivatives.

In an exemplary embodiment, the test card 2 is configured to be discarded after using. Alternatively, the test card 2 can be configured to be recycled to test more than one fluid sample.

Furthermore, an electrochemical sensor can be used in the test card 2 to detect blood gas, hemoglobin and its derivatives. The electrochemical detection technology is mature, which is not required to be described in detail.

Reagent Pack

Figure 9:
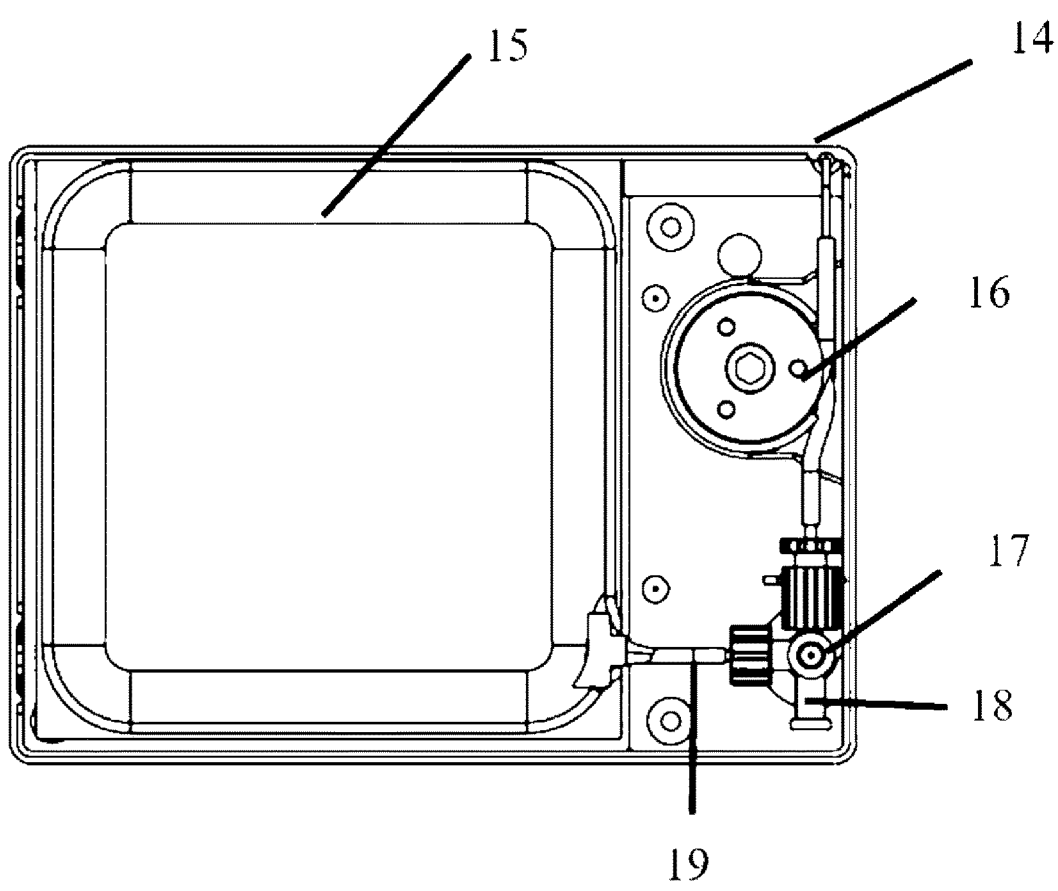
FIG. 9 is a schematic cross-sectional view of a removable reagent pack.
Figure 10:
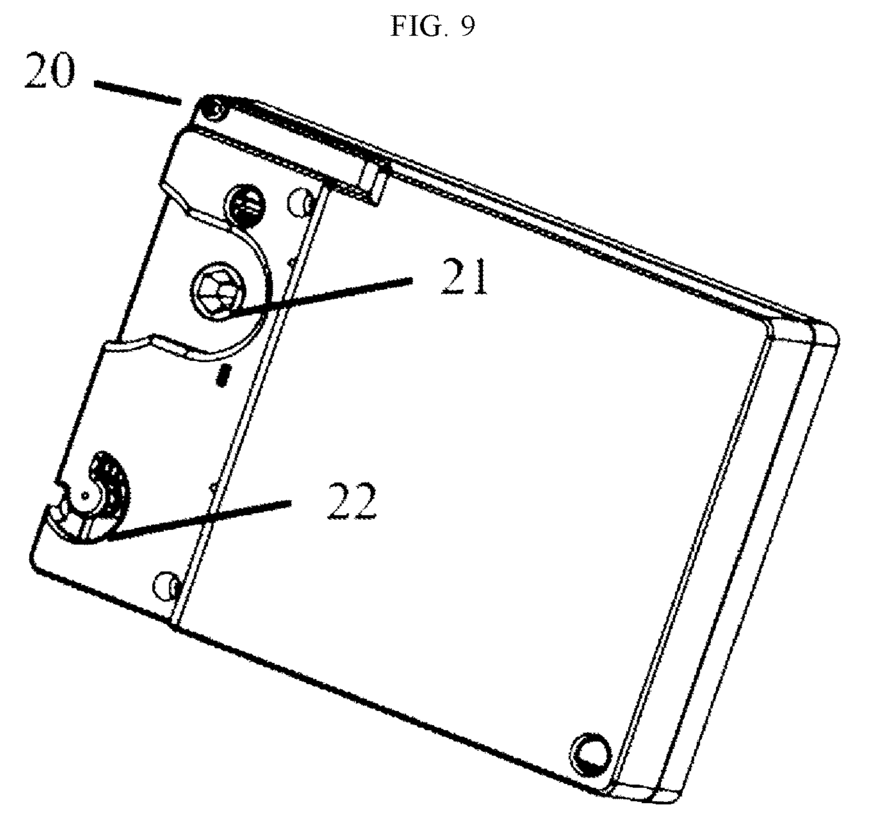
FIG. 10 is a schematic view of an external structure of the removable reagent pack.

As shown in FIG. 9, FIG. 9 is a schematic cross-sectional view of the reagent pack 3. The reagent pack 3 may be disposable and removable. The reagent pack 3 includes a housing 14, a calibration liquid bag 15, a peristaltic pump

16, a three-way valve 17, an air pipeline 18, and a calibration liquid pipeline 19, a connecting piece 20, a pump interface 21, and a valve connecting piece 22. The calibration liquid bag 15, the peristaltic pump 16, the three-way valve 17, the air pipeline 18, and the calibration liquid pipeline 19 are located in the housing 14. The connecting piece 20 is inserted into the calibration liquid inlet 6 of the test card 2. The pump interface 21 is connected to the shaft of the stepper motor of the host 1. The stepper motor drives the peristaltic pump 16 of the reagent pack 3 to forward rotate or reversely rotate through the pump interface 21. The host 1 controls the three-way valve 17 of the reagent pack 3 to switch through the valve connecting piece 22, thereby connecting the pump interface 21 to the air pipeline 18 or the calibration liquid pipeline 19. The calibration liquid bag 15 is configured to store the calibration liquid and is configured to be connected to the three-way valve 17 through the calibration liquid pipeline 19.

Figure 11:
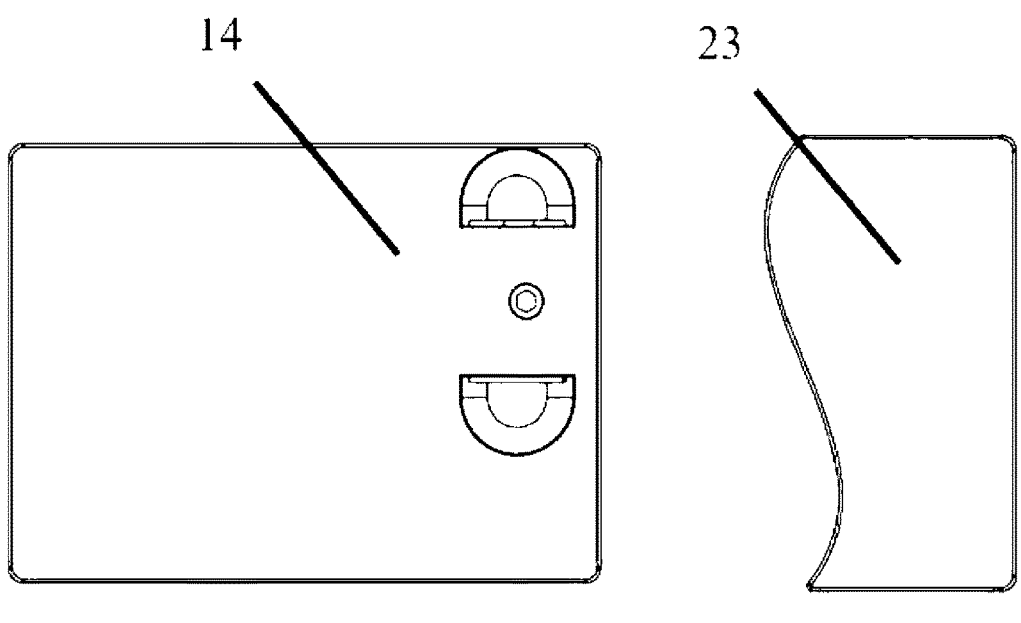
FIG. 11 is a schematic view of a body and a decoration cover of the removable reagent pack.
Figure 11:

In an exemplary embodiment, the housing 14 of reagent pack 3 is made of plastic, and can also be made of other materials or sets of materials. The reagent pack 3 can also include a decoration cover. As shown in FIG. 11, the decoration cover 23 of the reagent pack 3 is connected to the front part of the housing 14 of the reagent pack 3. When reagent pack 3 is not in use (i.e., not connected to the host 1), the decoration cover 23 of the reagent pack 3 can protect the housing 14 of reagent pack 3. The calibration liquid bag 15 can be an unused soft elastic fluid bag filled with the calibration liquid.

Before the test card 2 and the reagent pack 3 are respectively jointed with the host 1, the interior of the test card 2 is dry and has no calibration liquid, and the calibration liquid is completely stored in the reagent pack 3 and is separated from the test card 2.

When the test card 2 is placed in the first area 1*a*, the connecting piece 20 on the reagent pack 3 is inserted into the calibration liquid inlet 6 of the test card 2. In an embodiment, the connecting piece 20 is a tubular steel needle, and the circumference of the tubular steel needle is provided with a sealing ring, such as a rubber sealing ring, in order to ensure the sealing performance of the inserting position of the tubular steel needle and the calibrating liquid inlet 6 of the test card 2. After the calibration liquid is pumped into the test card 2, the calibration liquid cannot leak from the calibration liquid inlet 6. The controller in the host 1 controls the rotating shaft of the stepper motor to output power, and the peristaltic pump 16 in the reagent pack 3 is controlled to forward rotate or reversely rotate through the pump interface 21, so that the test card 2 can complete calibration and fluid sample detection, and the specific working principle is described in detail below.

When the test card 2 and the reagent pack 3 are respectively arranged in the first area 1*a* and the second area 1*b* of the host 1, the working principle of the reagent pack 3 is as follows.

When the calibration liquid in the reagent pack 3 needs to be output, such as, in the calibration stage of the test card 2 in the operation S2, the three-way valve 17 in the reagent pack 3 is switched to the calibration liquid pipeline 19 to be connected to the connecting piece 20. The peristaltic pump 16 is in a forward rotation state, so that the reagent pack 3 can output the calibration liquid outwards, and after the calibration liquid enters the test card 2, the photochemical sensor in the test card 2 is calibrated.

When air needs to be pumped to the outside, for example, when the calibration liquid and the detected blood sample are transferred to the waste liquid area 11 of the test card 2 in the operation S3 and the operation S5, or when the blood sample is transferred to the hemoglobin and its derivative detection area 8 after the blood gas detection is completed in the second stage of operation S4, the three-way valve 17 in the reagent pack 3 is switched to the air pipeline 18 to be connected to the connecting piece 20, the peristaltic pump 16 is in the forward rotation state, so that the reagent pack 3 can pump air into the test card 2, and the blood sample in the test card 2 can flow in the liquid path conducted in the test card 2 with the pumping of the air.

When air needs to be sucked into the reagent pack 3, for example, in the first stage of the operation S4, when the blood sample is sucked into the blood gas detection area 7 in the test card 2, the three-way valve 17 in the reagent pack 3 is switched to the air pipeline 18 to be connected to the connecting piece 20. The peristaltic pump 16 is in a reverse rotation state, so that the air in the test card 2 is sucked into the reagent pack 3, and the blood sample enters the liquid path in the test card 2 under the action of air pressure, thereby performing the blood gas detection.

Host

As previously described, the host 1 includes the housing, and the processing circuitry, the power supply circuitry, and the optical element are located in the housing. The housing may be plastic or any other material suitable for use in the present disclosure. The housing includes the first area 1*a* configured to at least partially accommodate the removable test card 2, and the second area 1*b* configured to at least partially accommodate the removable reagent pack 3. The removable test card 2 is jointed with the host 1 and the removable reagent pack 3 through the first area 1*a* and the second area 1*b*, respectively, thereby performing blood gas detection, hemoglobin and its derivative detection or other biochemical parameter detection. The test card 2 and the host 1 only have mechanical transmission connection, no liquid path connection. Only mechanical power transmission connection exists between the reagent pack 3 and the host 1, there is no liquid path connection between the reagent pack 3 and the host 1. The test card 2 is connected to the reagent pack 3 through the calibration liquid inlet 6, and calibration liquid flowing and air flowing are achieved. Due to above design mode, a liquid path system does not exist in the host 1, and liquid path flowing with the test card 2 and the reagent pack 3 is not needed.

In an exemplary embodiment, the first area 1*a* of the housing includes a test slot for accommodating the test card 2 containing the fluid sample, such as the blood sample. The syringe is configured to be connected to the sample inlet 4 of the test card 2. The host 1 is configured to test the fluid sample and report the result to the user through the output unit, for example, host 1 may include a display serving as the output unit. However, in this embodiment or other embodiments, diagnostic results may also or alternatively be reported to the user by other output units, including an audio output unit, a data communication output unit, or a print output unit, and so on.

In an exemplary embodiment, once the fluid sample is tested, the test card 2 may be removed from the host 1. The host 1 may include an ejection button, once the test is complete, the user can depress the ejection button to eject the test card 2 from the test slot. When the test cycle is completed, the host 1 may also be configured to automatically eject the test card 2. In an embodiment, the host 1 may be portable.

In an exemplary embodiment, the diagnostic results are displayed on the display. The processing circuitry of host 1 may cause the display to show information relating to a particular application. The display may be a unidirectional screen configured to display the output to the user, alternatively, the display may be a touch screen configured to receive and respond to the user's touch input. In an exemplary embodiment, the diagnostic device further includes a print slot configured to receive paper output by the printer housed within the host 1.

In an exemplary embodiment, as shown in FIG. 3, the second area 1*b* of the host 1 includes a reagent pack door configured to be opened from a side of the host 1. An opening behind the reagent pack door and the reagent pack door are configured to accommodate the reagent pack 3. The reagent pack door can be opened by a latch, or other mechanisms in another exemplary embodiment. The reagent pack door can also be located at other positions, for example, the reagent pack door may be located on either side, back, front or top of the host 1. The latch is adjacent to the reagent pack door, the power supply interface for supplying power to the pump from outside of the reagent bag, and the power supply interface for supplying power to the valve components.

In an exemplary embodiment, except for the connecting piece 20 of the reagent pack 3 directly connected to the calibration fluid inlet 6 of the test card 2, the reagent pack 3 and the host 1 can also be combined through the following methods. The connecting piece 20 of reagent pack 3 is connected to the host sample inlet above one side of host 1, and the host sample inlet is further connected to the calibration liquid inlet 6 of test card 2 to ensure that the calibration liquid can flow into the test card 2. The calibration liquid bag 15 of reagent pack 3 includes a bayonet groove, and the bayonet groove is configured to clamp onto the fixing device of reagent pack 3 on one side of host 1, in order to fix the reagent pack 3 in the second area 1*b* of host 1. The valve connecting piece 22 of reagent pack 3 is connected to the on-off valve control device of the reagent pack 3 on one side of host 1, thereby achieving on-off control of the three-way valve 17 of the reagent pack 3 by host 1. In addition, the pump interface 21 of reagent pack 3 is connected to the peristaltic pump control device on the side of host 1, such as the output shaft of the stepper motor, so that the host 1 can control the peristaltic pump 16 in the reagent pack 3.

In an exemplary embodiment, the host 1 may include one or more ports configured to accommodate a cable or other connection mechanism. The port can be configured to connect the host 1 to other pieces of the system (such as a communication network) or to upload or download information to the host 1. The host 1 can also be configured to exchange data wirelessly, including through Wi Fi (wireless internet technology), another wireless interact connection, or any other wireless information exchange. The host 1 can also include speakers configured to transmit noise or sound response to the user. The host 1 can also include a handle configured to hold the host 1. The handle rotates between two positions depending on whether it is used or not. In exemplary embodiments, the host 1 may also include a support leg configured to allow the host 1 to place on a desktop or other surface. In an exemplary embodiment, the host 1 may also include a barcode scanner installed on the side of host 1. The barcode scanner is configured to scan barcodes on the test card 2, calibration liquid bag 15, or any other items that have a scannable barcode and are used on the host 1. Barcode scanners can also be configured to scan barcode labels that represent patient or operator identities. In an exemplary embodiment, the barcode scanner emits a beam of light covering the barcode. When the barcode is successfully scanned, the host 1 emits a beep sound and the beam is automatically turn off. When the barcode is not successfully scanned, the host 1 alert the user by making noise or on the display through some other output unit. In exemplary embodiments, the barcode scanner is a one-dimensional barcode scanner. In other embodiments, the barcode scanner is a two-dimensional scanner.

According to an exemplary embodiment, the processing circuit of the host 1 includes an analog-to-digital converter and an analog control board. The analog-to-digital converter is configured to process an analog signal from the photochemical sensor, and transmits the processed digital signal to the analog control hoard. When the analog control boards herein and in the drawings are designated as "analog control board", the analog control board may include digital processing. Furthermore, the analog control board may utilize the digital-to-analog converter to convert the digital output (turn on/turn off modulated signal) to the analog signal (e.g., for the photochemical sensor).

The processing circuitry and power supply circuitry in the host 1 may be used as independent printed circuit board (PCB), integrated on the same PCB, or combined with integration and distribution. The processing circuit and the power supply circuit may include discrete components and/or integrated circuits. For example, the power supply circuit can include all discrete electronic components. The processing circuit may include one or more processors. The processor can be operated in multiple ways as a general-purpose processor, a specialized integrated circuit (ASIC), one or more field programmable gate arrays (FPGA), a set of processing components, or other suitable electronic processing components. The processing circuit may also include one or more memories. The memory can be one or more devices used to store data and/or computer code. The memory can be or include non-transient volatile memory and/or non-volatile memory. The memory may include a database component, an object code component, a script component, or any other type of information structure used to support various activities and the information structure described herein. The memory can be propagatively connected to the processor and includes computer code modules for executing one or more programs described herein.

The optical elements of the host 1 now are described in detail as previously described. In embodiments of the present disclosure, the blood gas parameters in the blood sample are measured by the photochemical sensor, and hemoglobin and its derivatives are detected using optical methods, such as colorimetry without the photochemical sensor. Thus, optical elements are needed to provide the light source, excite the photochemical sensor, transmit the optical signals, and the like.

Figure 12A:
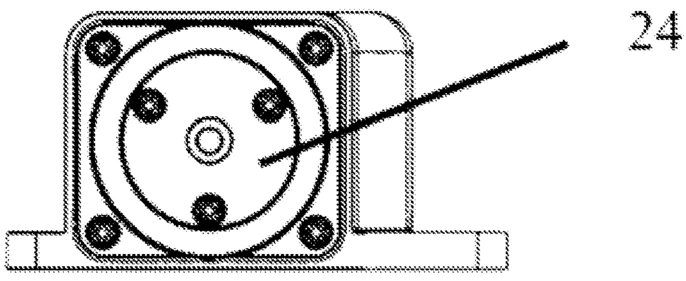
FIG. 12A is a schematic view of an excitation light source of the in-vitro medical diagnostic system.
Figure 12B:
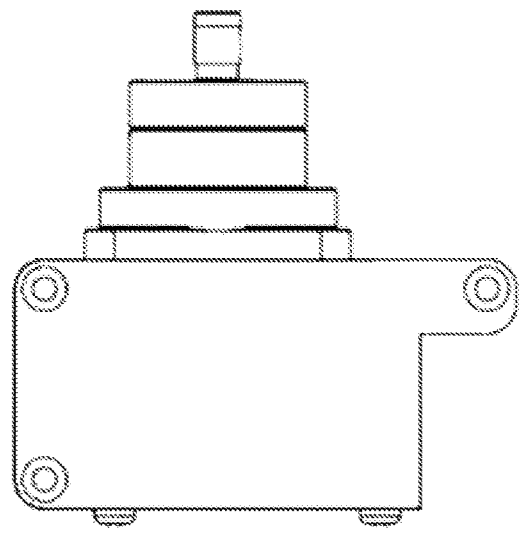
FIG. 12B is another schematic view of an excitation light source of the in-vitro medical diagnostic system.

Specifically, the optical element of the host 1 includes two parts. The first part is arranged in the host 1, and the first part includes a first light source for detecting the hemoglobin and its derivatives and a second light source for detecting the fluid position of the test card 2. The different detection beams are emitted to detect the presence or absence of fluid in the hemoglobin and its derivatives of the blood sample and in each position monitoring point of the test card 2, respectively. The second part is arranged in the host 1, and equipped with a light source 24 for optically detecting the blood gas component of the Hood sample, as shown in FIG. 12A and FIG. 12B. Specifically, the light source 24 is an excitation light source 24 configured to emit an excitation beam to excite the photochemical sensor in the test card 2, and the excitation light source is located within the host 1 and is lower in height than the first area 1*a*.

In an exemplary embodiment, the diagnostic device includes the valve control mechanism configured to control the valve component of the test card 2.

The beneficial effect of the present disclosure lies in, the removable reagent pack of the in-vitro diagnostic device can exist entirely independent of the host and test card of the in-vitro diagnostic system, suitable for independent transportation and storage. The pump and the valve parts of the removable reagent pack enable the reagent pack to be well matched with the test card of the in-vitro diagnostic device to complete pumping of calibration liquid, evacuating the calibration liquid, withdrawing a fluid sample into the test card interior, so that the detections of blood gas, hemoglobin and its derivatives thereof and other biochemical parameters are completed. The reagent pack can be reused many times because the reagent pack has a readable device that can read factory information and use status, making it easy for operators to promptly know the status of the reagent pack. It can greatly prevent waste of the calibration liquid, reduce the use cost of calibration liquid reagent pack, and the operator can be assisted to better respond to the in-vitro diagnosis.

The terms "generally", "about" "substantially", and similar terms used here have a broad meaning consistent with the generally accepted usage recognized by those skilled in the art, and the subject of this disclosure belongs to the generally accepted usage. Those skilled in the art who review this disclosure should understand that these terms are intended to allow descriptions of certain features described and claimed, without limiting the scope of these features to a set precise numerical range. Therefore, these terms should be interpreted as non-substantive or incoherent modifications or modifications of the subject matter described and claimed priority should be considered within the scope of the present disclosure and explained by the accompanying claims. It should be noted that the term "exemplary" used in this disclosure to describe different embodiments refers to possible examples, illustrations representing and/or possible embodiments (this term does not imply that such embodiments must be extraordinary examples or highest-level examples). The terms "coupled" and "connected" and their analogues used in this disclosure refer to the direct or indirect combination of two components with each other. This combination can be static (such as permanent) or movable (such as removable or releasable). This combination can be achieved by combining two components or integrating the terrain into a single entity with any additional intermediate components, or by combining two components or two components attached to each other with any additional intermediate components. The structure and arrangement of the system and the methods for providing in-vitro medical diagnostic devices as shown in various exemplary embodiments are just illustrated.

Only some embodiments have been described in detail in present disclosure, but it will be readily appreciated by those skilled in the art with reference to this disclosure, there may be many modifications (e.g., variations in size, structure, shape and scale of various elements, parameter values, mounting arrangements, use of materials, color, changes in orientation, and so on) without substantially departing from the novel teachings and advantages of the subject matter disclosed herein. For example, the components shown as a whole can be composed of multiple parts or components, and the position of the components can be reversed or otherwise changed, as well as the nature, quantity, or position of discrete components can be changed. All such modifications are intended to be included in the scope of the present disclosure as defined in the appended claims. The order or sequence of any process or method step can be changed or reordered according to alternative embodiments. The design, operating conditions, and arrangement of various exemplary embodiments can be replaced, modified, altered, and omitted without departing from the scope of the present disclosure.

The diagnostic device is generally shown to include the processing circuitry including the memory. The processing circuitry may include the processor. The processor can be operated as a general-purpose processor, a specialized integrated circuit (ASIC), one or more field programmable gate arrays (FPGA), a set of processing components, or other suitable electronic processing components. The memory can be one or more devices configured to store data and/or computer code (e.g., RAM, ROM, flash memory, hard disk memory, or the like), to complete and/or implement various programs described in present disclosure. The memory can be or include non-transient volatile memory and/or non-volatile memory. The memory may include the database component, the object code component, the script component, or any other type of information structure used to support various activities and the information structure described herein. The memory can be propagatively connected to the processor and includes computer code modules for executing one or more programs described herein. The foregoing is merely a preferred embodiment of the present disclosure, without limiting the disclosure, any modifications, equivalents, substitutions, and modifications made within the spirit and principles of the disclosure should be included within the scope of the disclosure.

What is claimed is:

1. A removable reagent pack for use in an in-vitro diagnostic device, the removable reagent pack being removably engaged with a test card and a host, the removable reagent pack comprising:

a housing;

at least one external interface located on the housing;

at least one liquid storage device comprising an output pipeline, wherein the at least one liquid storage device is located in a space formed by the housing;

a pump located in the space, wherein the pump is configured to control at least a flow direction in a pipeline inside of the removable reagent pack, so that a liquid inside of the at least one liquid storage device flows out through the output pipeline; and at least one positioning mechanism connected to the pump, so that the pump is driven by the in-vitro diagnostic device.

2. The removable reagent pack as claimed in claim 1, wherein the pump is configured to be forward rotated and/or reverse rotated.

3. The removable reagent pack as claimed in claim 1, wherein the pump is a peristaltic pump.

4. The removable reagent pack as claimed in claim 1, further comprising at least one pipeline switching device.

5. The removable reagent pack as claimed in claim 4, further at least comprising three pipelines: a first pipeline being the output pipeline of the liquid storage device, a second pipeline connected to an exterior, and a third pipeline connected to the at least one external interface of the removable reagent pack; wherein the pipeline switching device is configured to allow one of the first pipeline and the second pipeline to be connected to the third pipeline.

6. The removable reagent pack as claimed in claim 5, wherein the pump is located on at least the third pipeline.

7. The removable reagent pack as claimed in claim 1, wherein the at least one external interface is configured to output liquid in the removable reagent pack, output gas and/or input gas.

8. The removable reagent pack as claimed in claim 1, wherein the external interface is at least partially encapsulated with a seal.

9. The removable reagent pack as claimed in claim 1, wherein the liquid is a calibration liquid.

10. The removable reagent pack as claimed in claim 1, wherein the positioning mechanism is a groove.

11. A method for controlling the removable reagent pack as claimed in claim 1, comprising:

a first stage, configuring the pump to allow a removable reagent pack to outwardly output quantitative calibration liquid;

a second stage, configuring the pump to allow the removable reagent pack to outwardly output a quantitative gas;

a third stage, configuring the pump to allow an exterior to input a quantitative gas into the removable reagent pack; and a fourth stage, configuring the pump to allow the removable reagent pack to outwardly output a quantitative gas.

12. The method as claimed in claim 11, wherein the first stage is a stage that a sensor is calibrated by the test card or the host.

13. The method as claimed in claim 11, wherein the second stage is a stage of emptying the calibration liquid after completing a calibration.

14. The method as claimed in claim 11, wherein the third stage is a stage that a sample to be detected is injected into the test card for blood gas detection.

15. The method as claimed in claim 12, wherein the fourth stage is a stage that a sample to be detected in the test card is transferred from a blood gas detection area to a hemoglobin and its derivatives detection area.

16. The method as claimed in claim 11, wherein based on the same sample to be detected in the test card, a blood gas detection is performed in the third stage, and a detection of hemoglobin and its derivatives is performed in the fourth stage.

17. The method as claimed in claim 11, wherein in the first stage, the second stage and the fourth stage, the pump is configured to receive a forward driving force output by the host of the in-vitro diagnostic device; and in the third phase, the pump is configured to receive a reverse driving force output by the host of the in-vitro diagnostic device.

18. The method as claimed in claim 11, wherein in the first stage, a pipeline switching device in the removable reagent pack is configured to connect an output pipeline of a liquid storage device to at least one external interface; and in the second stage to the fourth stage, the pipeline switching device is configured to connect a gas source to the at least one external interface.

19. The removable reagent pack as claimed in claim 1, wherein the at least one positioning mechanism is connected to a shaft of a stepper motor of the host so that the pump is driven by the shaft of the stepper motor.

20. A removable reagent pack for use in an in-vitro diagnostic device, comprising:

a housing;

at least one external interface located on the housing;

at least one liquid storage device comprising an output pipeline, wherein the at least one liquid storage device is located in a space formed by the housing;

a pump located in the space, wherein the pump is configured to control at least a flow direction in a pipeline inside of the removable reagent pack, so that a liquid inside of the at least one liquid storage device flows out through the output pipeline; and a groove connected to the pump, wherein the groove is connected to a shaft of a stepper motor of a host so that the pump is driven by the shaft of the stepper motor.

* * * * *